United States Patent [19]

Wollensak et al.

[11] 4,317,931

[45] Mar. 2, 1982

[54] PROCESS FOR REARRANGEMENT OF ALKYL GROUPS ON AROMATIC AMINES

[75] Inventors: John C. Wollensak, Bloomfield Hills; Kryn G. Ihrman, Farmington; Chester P. Jarema, Sterling Heights, all of Mich.

[73] Assignee: Ethyl Corporation, Richmond, Va.

[21] Appl. No.: 240,752

[22] Filed: Mar. 5, 1981

Related U.S. Application Data

[63] Continuation-in-part of Ser. No. 72,931, Sep. 6, 1979, abandoned.

[51] Int. Cl.³ ............................................. C07C 85/24
[52] U.S. Cl. ................................................... 564/409
[58] Field of Search ........................................ 564/409

[56] References Cited

U.S. PATENT DOCUMENTS

| | | | |
|---|---|---|---|
| 2,814,646 | 11/1957 | Kolka et al. | 564/409 |
| 3,275,690 | 9/1966 | Stroh et al. | 564/409 |
| 3,417,149 | 12/1968 | Neuworth et al. | 568/804 |
| 3,418,380 | 12/1968 | Laufer et al. | 568/784 |
| 3,649,693 | 3/1972 | Napolitano | 564/409 |
| 3,674,852 | 7/1972 | Averill et al. | 564/409 |
| 3,761,520 | 9/1973 | Napolitano | 564/409 |
| 3,923,892 | 12/1975 | Klopfer | 564/409 |
| 3,933,927 | 1/1976 | Goddard | 568/780 |
| 4,128,582 | 12/1978 | Governale et al. | 564/409 |

OTHER PUBLICATIONS

Kirk–Othmer, "Encyclopedia of Chemical Technology," vol. 5, 2nd Ed., p. 740 and 744, (1964); vol. 20, 2nd Ed., p. 486, (1965).

Groggins, "Unit Processes in Organic Synthesis," 5th Ed., p. 807, (1958).

Ogata et al, "Chemical Abstracts," vol. 62, pp. 2687–2688, (1965).

Olah, "Friedel–Crafts and Related Reactions," vol. II, Part 1, pp. 531–533, (1964).

*Primary Examiner*—Robert V. Hines
*Attorney, Agent, or Firm*—Donald L. Johnson; Joseph D. Odenweller; John F. Hunt

[57] ABSTRACT

Methyl groups on o-methyl aromatic amine are redistributed to ortho positions by heating in contact with an aluminum anilide catalyst and a nickel, cobalt, molybdenum or titanium-containing cocatalyst. For example, o-toluidine forms a mixture containing an aniline, o-toluidine, 2,6-dimethylaniline, and 2,4-dimethylaniline.

11 Claims, No Drawings

PROCESS FOR REARRANGEMENT OF ALKYL GROUPS ON AROMATIC AMINES

CROSS REFERENCE TO RELATED APPLICATION

This application is a Continuation-in-Part of application Ser. No. 72,931, filed Sept. 6, 1979 and now abandoned.

BACKGROUND OF THE INVENTION

Aromatic amines can be alkylated selectively in an ortho position by reaction with an olefin in the presence of an aluminum anilide catalyst. Such reactions are described in Kolka et al, U.S. Pat. Nos. 2,814,646; Stroh et al, 3,275,690; Klopfer, 3,923,892 and Governale et al, 4,128,582. It is also known that tert-alkyl groups on phenols can be redistributed using sulfuric acid catalysts, cf U.S. Pat. No. 3,418,380. Similarly, methyl groups on phenols have been redistributed using an alumina catalyst, cf U.S. Pat. No. 3,417,149. Transalkylation of phenol by sec-alkyl and tert-alkyl phenols using an aluminum phenoxide catalyst is described in U.S. Pat. No. 3,933,927.

SUMMARY

According to the present invention, o-methyl groups on o-methyl aromatic amines are redistributed to unsubstituted positions on aromatic amines by heating the o-methyl aromatic amine in the presence of an aluminum anilide-type catalyst and a metal-containing cocatalyst wherein the metal is nickel, cobalt, molybdenum or titanium.

Although it is an object of this invention to form 2,6-dimethylaniline, it has been found that varying proportions of both 2,6- and 2,4-dimethylaniline are formed by the inventive process depending on the catalysts, starting materials used, as well as the type of reaction vessel.

DESCRIPTION OF THE PREFERRED EMBODIMENTS

A preferred embodiment of the invention is a process for redistributing methyl groups on nuclear methyl-substituted aromatic amines, said process comprising heating an aromatic amine or mixture of aromatic amines, said aromatic amine or mixture of aromatic amines containing (a) aromatic amine having at least one o-methyl substituent and (b) aromatic amine having at least one ortho position unsubstituted except for hydrogen, at a temperature of about 100°–500° C. in the presence of an aluminum anilide catalyst and a metal-containing cocatalyst, said metal being selected from nickel, cobalt, molybdenum and titanium.

The aromatic amines which are subject to the redistribution reaction can be a single aromatic amine or a mixture of aromatic amines. If it is a single aromatic amine it must have an o-methyl substituent and an unsubstituted ortho position. Other positions may be unsubstituted or substituted with groups such as alkyl, halide and the like. When using a single aromatic amine the preferred compound is o-toluidine. When heated in the presence of an aluminum anilide-type catalyst and a nickel, cobalt, molybdenum or titanium containing cocatalyst, o-toluidine redistributes methyl groups according to the following reaction:

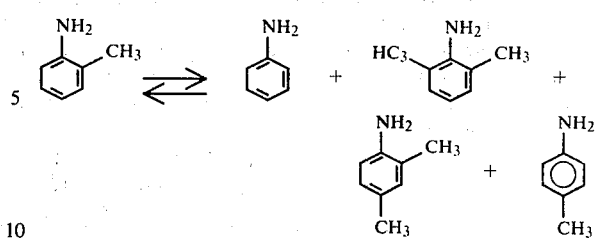

The equilibrium for the reaction favors o-toluidine. However, aniline may be distilled out shifting the equilibrium to the right, increasing the formation of 2,6-dimethylaniline and 2,4-dimethylaniline.

In the event that 2,6-dimethylaniline is in good supply, it can be used as a source of methyl groups to be redistributed to the other aromatic amines having unsubstituted ortho positions. Examples of aromatic amines having unsubstituted ortho positions are aniline, o-ethylaniline, α-naphthylamine, β-naphthylamine, p-chloroaniline and the like.

Tri-substituted aniline can be used as a source of methyl groups. An example of such a donor compound is 2,4,6-trimethylaniline. In this case, the p-methyl group does not migrate to any extent.

Aluminum anilide-type catalysts useful in the process include those used to ortho alkylate aromatic amines as described in U.S. Pat. Nos. 2,814,646; 3,275,690; 3,923,892 and 4,128,582.

The aluminum trianilides are readily made by reacting aluminum metal, aluminum hydride or aluminum tri-lower alkyl with an aromatic amine. This can be carried out by adding the aluminum or aluminum compound to the aromatic amine and heating under a nitrogen atmosphere until an exothermic reaction occurs. This is conducted in an autoclave which can withstand at least 1000 psig. When aluminum alkyls are used to prepare the catalyst care should be taken in handling these materials because of their pyrophoric nature. Aluminum alkyls react with aromatic amines at farily low temperatures from about ambient temperature up to about 150° C. Aluminum metal generally requires heating the mixture to about 200°–300° C. Once the catalyst formation starts it proceeds rapidly. Examples of aluminum trianilide are aluminum trianilide, aluminum tri-(2-methylanilide), aluminum tri-(p-chloroanilide), aluminum tri-(2,4-dimethylanilide) and the like.

A second class of aluminum anilide-type catalysts are the above aluminum trianilides in combination with a Friedel-Crafts promoter such as aluminum chloride, aluminum bromide, stannic chloride, boron trifluoride and the like.

A third class of aluminum anilide-type catalysts are the catalysts formed by reacting an alkyl aluminum halide with an aromatic amine. Suitable alkyl aluminum halides for forming the catalysts are diethyl aluminum chloride, ethyl aluminum dichloride, ethyl aluminum sesquichloride, methyl aluminum sesquichloride and the like.

A fourth type of aluminum anilide-type catalysts are the hydrogen halide promoted aluminum anilides. In this class a hydrogen halide is added to the previously described aluminum trianilide-type catalyst to promote the catalyst. Of the hydrogen halides, hydrogen chloride is preferred. An amount sufficient to provide about 0.1–2 gram atoms of chloride per gram atom of aluminum is a useful ratio.

The amount of aluminum anilide-type catalyst added to the aromatic amine can vary over a wide range. A useful range is that amount which provides about 0.005–0.5 gram atom of aluminum per mole of aromatic amines. A more preferred range is about 0.1–0.25 gram atom of aluminum per mole of aromatic amine.

The metal-containing cocatalysts are those which contain nickel, cobalt, molybdenum or titanium. Examples of these are nickel carbonate, cobalt naphthenate, molybdenum naphthenate and titanium tetraalkoxide such as tetraisopropoxide, tetrabutoxide, tetradecoxide and the like. Other representative examples of these cocatalysts are nickel chloride, nickel bromide, nickel sulfate, cobaltic chloride, titanium trichloride, titanium tetrachloride, nickel naphthenate, nickel acetate, nickel oleate, nickel metal, cobaltic acetate, cobaltous bromide, cobaltous oxalate, cobalt metal, titanium bromide and the like.

The amount of cocatalysts can vary over a wide range. A useful concentation is that which provides about 0.005–0.5 moles per mole of aromatic amine. A more preferred range is 0.01–0.02 moles per mole of aromatic amine.

The redistribution reaction is carried out by adding the catalyst precursor to the o-methyl aromatic amine or mixture of aromatic amines as previously described. This is heated under nitrogen to form the aluminum anilide catalyst prior to adding the metal cocatalyst or the metal cocatalyst can be added prior to heating. In either event, the heating is conducted under an inert atmosphere such as nitrogen in a sealed autoclave. After the aluminum anilide-type catalyst forms the autoclave is cooled and vented although venting is not required. The autoclave is then sealed and heated to reaction temperature. An elevated temperature is required. A useful range for carrying out the redistribution reaction is about 200°–500° C. A preferred temperature range is about 300°–400° C.

The following examples serve to illustrate the manner in which the process is conducted.

At the time the following experimental examples were run, it was thought that 2,6-dimethylaniline was formed without the production of 2,4-dimethylaniline. Further studies and additional analysis techniques have indicated the presence of 2,4-dimethylaniline as a minor proportion of the dimethylaniline formed. In the following examples, only "dimethylaniline" content of the reaction product is reported. For these examples the proportion of 2,6- to 2,4-dimethylaniline is about 2:1. That ratio varies with reactants, their purity, the catalyst, and the reaction vessel.

EXAMPLE 1

In an autoclave was placed 107.2 grams of o-toluidine, 4.6 grams aluminum granules and 0.99 gram nickel carbonate. The autoclave was flushed with nitrogen and heated to 300° C. An exothermic reaction occurred indicating catalyst formation. Heating was continued to 350° C. and the reaction was held at 350° C. with stirring for 4.25 hours. Pressure was 890 psig. The reaction was then cooled, vented and analyzed by vapor phase chromatography (VPC) to contain 23% aniline, 71% o-toluidine, and 5.9% dimethylaniline. These products can be separated by distillation.

EXAMPLE 2

In an autoclave was placed 107.2 grams of o-toluidine and 1.2 grams nickel carbonate. The autoclave was flushed with nitrogen and then 22.6 grams (27 ml) of triethyl aluminum was added. The autoclave was sealed and heated. At 150° C. a pressure jump was observed indicating catalyst formation. The autoclave was cooled and vented. It was again sealed and heated rapidly to 150° C. and slowly to 350° C. It was stirred at 350° C. for 1 hour following which a sample was removed and analyzed by VPC. Its composition was 20.3% aniline, 69.3% o-toluidine, 3.3% dimethylaniline and 7.6% high boiling products.

EXAMPLE 3

In an autoclave was placed 107.2 grams of o-toluidine, 5.4 grams aluminum granules and 5.3 grams molybdenum naphthenate. The autoclave was flushed with nitrogen, sealed, and while stirring, heated to 330° C. over one hour. It was stirred at 330° C. for 35 minutes and then cooled and vented. It was resealed and heated to 330° C. and maintained at that temperature for 22 hours. It was then cooled and the product analyzed by VPC. It contained 1% aniline, 95% o-toluidine, and 4% dimethylaniline.

EXAMPLE 4

In an autoclave was placed 107.2 grams of o-toluidine, 5.4 grams aluminum granules and 3.4 grams titanium tetrabutoxide. The autoclave was flushed with nitrogen, sealed and heated to 330° C. Pressure rose to 840 psig. It was cooled and vented to remove a sample. It was sealed and reheated to 330° C. and stirred at that temperature for about 5 hours. It was then cooled and vented and analyzed by VPC. It contained 0.5% aniline, 91% o-toluidine, 2.6% dimethylaniline and 5.7% toluene.

EXAMPLE 5

In an autoclave was placed 107.2 grams of o-toluidine, 5.4 grams aluminum granules and 10 grams cobalt naphthenate (0.6 g cobalt). The autoclave was sealed and heated to 330° C. causing a pressure jump to 860 psig. The autoclave was cooled and vented. It was resealed and heated to 330° C. and stirred at that temperature for 18.5 hours. It was then cooled and vented and the product analyzed by VPC. It contained 8.7% aniline, 53.8% o-toluidine, 8.6% dimethylaniline and 7.4% high boiling products.

EXAMPLE 6

In an autoclave was placed 107.2 grams o-toluidine and 5.4 grams aluminum granules. The autoclave was flushed with nitrogen and heated to 330° C. The temperature jumped to 380° C. at 800 psig. The autoclave was stirred for 30 minutes at 330° C. and then cooled and vented. Then 10 grams of colbalt naphthenate (0.6 gram cobalt) was added and the autoclave again heated to 330° C. It was stirred at that temperature for 2 hours following which it was cooled and vented. It was sealed and reheated to 330° C. and stirred at that temperature for 2 hours. It was then cooled, vented and discharged. A strong ammonia odor was noted. Analysis by VPC showed benzene 7%, toluene 8%, aniline 15%, o-toluidine 48%, and dimethylaniline 16%.

The aromatic amines made by this process are useful chemicals. One important use is as an intermediate in the production of herbicides and fungicides such as those described in U.S. Pat. Nos. 3,853,531; 3,859,308; 3,885,952; 3,888,882; 4,001,325 and 4,025,554.

We claim:

1. A process for redistributing methyl groups on nuclear methyl-substituted aromatic amines, said process comprising heating an aromatic amine or mixture of aromatic amines, said aromatic amine or mixture of aromatic amines containing (a) aromatic amine having at least one o-methyl substituent and (b) aromatic amine having at least one ortho position unsubstituted except for hydrogen, at a temperature of about 100°–500° C. in the presence of an aluminum anilide catalyst and a metal-containing cocatalyst, said metal being selected from nickel, cobalt, molybdenum and titanium.

2. A process of claim 1 wherein said aromatic amine or mixture of aromatic amines consists mainly of o-toluidine.

3. A process of claim 2 wherein said aluminum anilide catalyst is aluminum tri-(o-methyl anilide) and said cocatalyst is a nickel compound.

4. A process of claim 3 wherein said nickel compound is nickel carbonate.

5. A process of claim 2 wherein said aluminum anilide catalyst is aluminum tri-(o-methyl anilide) and said cocatalyst is a cobalt compound.

6. A process of claim 5 wherein said cobalt compound is cobalt naphthenate.

7. A process of claim 2 wherein said aluminum anilide catalyst is aluminum tri-(o-methyl anilide) and said cocatalyst is a molybdenum compound.

8. A process of claim 7 wherein said molybdenum compound is molybdenum naphthenate.

9. A process of claim 2 wherein said aluminum anilide catalyst is aluminum tri-(o-methyl anilide) and said cocatalyst is a titanium compound.

10. A process of claim 9 wherein said titanium compound is a titanium tetraalkoxide.

11. A process of claim 10 wherein said titanium tetraalkoxide is titanium tetrabutoxide.

* * * * *